United States Patent [19]

Rösner et al.

[11] Patent Number: 4,639,463

[45] Date of Patent: Jan. 27, 1987

[54] SUBSTITUTED PHENYLSULFONYLOXYBEN-ZIMIDAZOLECARBAMATES AND ANTHELMINTIC COMPOSITIONS

[75] Inventors: Manfred Rösner, Eppstein; Heinz Loewe, Kelkheim; Dieter Düwel, Hofheim am Taunus; Reinhard Kirsch, Eppstein, all of Fed. Rep. of Germany

[73] Assignee: Hoechst Aktiengesellschaft, Fed. Rep. of Germany

[21] Appl. No.: 563,780

[22] Filed: Dec. 21, 1983

[30] Foreign Application Priority Data

Dec. 23, 1982 [DE] Fed. Rep. of Germany ....... 3247615

[51] Int. Cl.$^4$ ................ A61K 31/415; C07D 403/30; C07D 235/04; C07D 471/00
[52] U.S. Cl. .................................... 514/395; 548/315; 548/329; 546/87
[58] Field of Search .................. 548/315, 329; 546/87; 514/395

[56] References Cited

U.S. PATENT DOCUMENTS 3,996,368  12/1976  Loewe et al. .................. 548/306

FOREIGN PATENT DOCUMENTS 612726   9/1975   Belgium .......................... 424/300
562096   8/1958   Canada ............................ 424/300
0054507  12/1981  Fed. Rep. of Germany ...... 424/300
764232   12/1956  United Kingdom ............... 424/300

OTHER PUBLICATIONS

Astopof, U.S.S.R., col. 1-2, p. 726097.

Primary Examiner—Henry R. Jiles
Assistant Examiner—Robert C. Whittenbaugh
Attorney, Agent, or Firm—Finnegan, Henderson, Farabow, Garrett & Dunner

[57] ABSTRACT

New phenylsulfonyloxybenzimidazolecarbamates of the formula

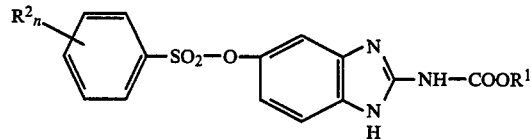

are described, as are processes for their preparation. The new compounds have anthelmintic activity, including, in particular, against liver flukes.

15 Claims, No Drawings

SUBSTITUTED PHENYLSULFONYLOXYBENZIMIDAZOLECARBAMATES AND ANTHELMINTIC COMPOSITIONS

The present invention relates to new substituted phenylsulfonyloxybenzimidazolecarbamates, processes for their preparation and their use as medicaments, especially as anthelmintics.

Phenylsulfonyloxybenzimidazolecarbamates having anthelmintic actions are known from U.S. Pat. No. 3,996,368.

A new group of substituted phenylsulfonyloxybenzimidazolecarbamates having anthelmintic activity, of the formula I

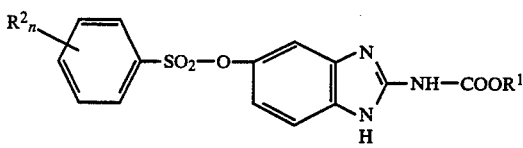

in which $R^1$ denotes straight-chain or branched alkyl having 1–4 carbon atoms, n denotes 1 or 2, and the individual substituents $R^2$, independently of one another, denote fluorine, bromine, 1,1,2,2-tetrafluoroethoxy, alkyl having 2 to 4 carbon atoms or cycloalkyl having 3–8 carbon atoms, has now been found.

Among the compounds of the formula I, those are preferred in which $R^1$ denotes methyl, n denotes 1 or 2, and $R^2$ denotes fluorine, bromine, 1,1,2,2-tetrafluoroethoxy, ethyl, n-propyl, isopropyl or cycloalkyl having 5, 6 or 7 carbon atoms.

Those compounds of the formula I in which $R^1$ denotes methyl, n denotes 1, and $R^2$ denotes fluorine, 1,1,2,2-tetrafluoroethoxy, n-propyl, isopropyl or cycloalkyl having 5, 6 or 7 carbon atoms are very particularly preferred.

The invention also relates to processes for the preparation of substituted phenylsulfonyloxybenzimidazolecarbamates of the formula I, which comprises (a) reacting, with ring closure, an o-phenylenediamine derivative of the formula II

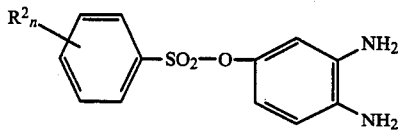

in which n and $R^2$ have the meanings indicated for formula I, with a carbamic ester derivatives of the formula III

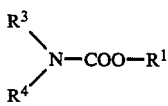

in which $R^1$ has the meaning indicated for formula I, and $R^3$ denotes CN, and $R^4$ denotes hydrogen, or $R^3$ and $R^4$ together denote one of the following radicals double-bonded to the nitrogen atom

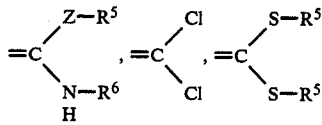

in which $R^5$ denotes alkyl having 1–4 carbon atoms, $R^6$ denotes hydrogen or —$COOR^1$, and Z denotes oxygen or sulfur, or (b) reacting a benzimidazolecarbamate of the formula IV

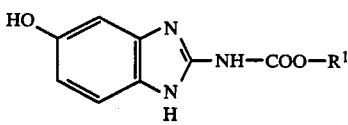

with a substituted benzenesulfonyl halide of the formula V

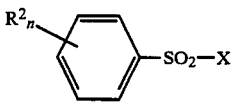

in which $R^1$, $R^2$ and n have the meanings indicated for formula I, and X denotes fluorine, chlorine, bromine or iodine, or (c) reacting a 2-aminobenzimidazole of the formula VI

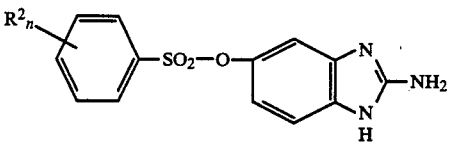

with a carbonic ester derivative of the formula VII

in which $R^1$, $R^2$ and n have the meanings indicated above, and Y represents —$OR^1$ or chlorine.

The substituted o-phenylenediamines of the formula II used as starting materials for process (a) are obtained by reduction of nitroamino compounds of the formula VIII

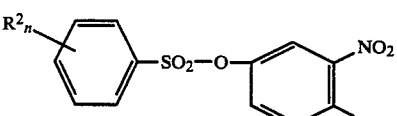

in which n and $R^2$ have the meanings indicated above.

The preparation of nitroamines of the formula VIII is described in U.S. Pat. No. 3,996,368.

It takes place by reacting a substituted benzenesulfonyl halide of the formula V with 4-amino-3-nitrophenol or its salts in an inert solvent, such as, for example, acetone, in the presence of an organic or inorganic base, such as, for example, triethylamine or sodium hydroxide. The compounds of the formula V are either known from the literature or they can be prepared in analogy to known compounds by known processes (cf. Houben-Weyl, Methoden der Organischen Chemie (Methods of Organic Chemistry), Volume 9, pages 561–587, Stuttgart 1955).

The nitroamino compounds of the formula VIII are hydrogenated to give a diamino compound of the formula II by reduction, advantageously with catalytically activated hydrogen, for example with Raney nickel, platinum or palladium catalysts, in a solvent, such as methanol, 2-methoxyethanol or dimethylformamide or their mixtures, under atmospheric pressure or under a pressure of 1–3 atmospheres.

For carrying out process (a), a diamine of the formula II or one of its salts is reacted with a compound of the formula III. The compounds of the formula III are known.

When, in formula III, $R^3$ denotes CN and $R^4$ denotes hydrogen, then, advantageously, an o-phenylenediamine derivative of the formula II is added to an aqueous solution of the cyanamidecarboxylate of the formula III, the pH is adjusted to 1–6, preferably 2–5, by the addition of an inorganic or organic acid, for example hydrochloric acid or glacial acetic acid, and the reaction is advantageously carried out between 20° and 100° C. The reaction time is between 30 minutes and 10 hours depending on the reactivity of the compound of the formula II.

When, in formula III, $R^3$ and $R^4$ together denote

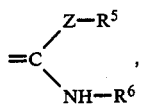

in which $R^5$, $R^6$ and Z have the meanings indicated above, the reaction with o-phenylenediamines of the formula II is carried out in a suitable solvent in a temperature range from 0° to 150° C., preferably at the boiling point of the reaction mixture, and with the addition of an inorganic or organic acid, such as hydrochloric acid, sulfuric acid, formic acid, glacial acetic acid or p-toluenesulfonic acid. Examples of suitable solvents are: water, methanol, ethanol, isopropanol, amyl alcohol, glycol monomethyl ether, dioxane, tetrahydrofuran, diethyl ether, diisopropyl ether, dimethoxyethane, toluene, xylene, glacial acetic acid, acetone, butanone, methylene chloride or chloroform. Depending on the type of the substituents and the reaction conditions, the reaction times can be between about 30 minutes and 10 hours.

When $R^3$ and $R^4$ in formula III together denote

then the N-dichloromethylenecarbamic ester of the formula III and the o-phenylenediamine derivative of the formula II are advantageously reacted in a suitable solvent in the presence of at least two equivalents of an inorganic or organic base, such as, for example, sodium hydroxide, sodium bicarbonate, potassium carbonate, triethylamine or pyridine.

Examples of suitable solvents are toluene, xylene, diethyl ether, diisopropyl ether, dioxane, tetrahydrofuran, dimethoxyethane, methylene chloride, chloroform, dichloroethane, acetone or butanone. The temperature used is −20° to +80° C., preferably between 0° and 30° C.

When $R^3$ and $R^4$ in formula III together denote

in which $R^5$ has the meaning given above, then the compound of the formula III is reacted with a compound of the formula II, for example in diisopropyl ether, dioxane, tetrahydrofuran, dimethoxyethane, chloroform, dichloroethane, toluene, xylene, acetone or butanone, at elevated temperature, advantageously at the boiling point of the solvent employed.

In an advantageous manner, a nitroamino compound of the formula VIII is reduced as described to give a substituted o-phenylenediamine II, the catalyst is separated off, the solution of the diamine of the formula II is concentrated under reduced pressure, and the residue is directly reacted with a compound of the formula III as described to give a compound of the formula I.

To carry out process (b), a hydroxybenzimidazolecarbamate of the formula IV is reacted, in an aprotic solvent, such as, for example, acetone, dioxane or dimethylformamide, with a substituted benzenesulfonyl halide of the formula V, in the presence of an organic or inorganic base, such as triethylamine, potassium carbonate or sodium hydroxide, at 0°–50° C.

The 2-aminobenzimidazoles of the formula VI, in which the substituents have the meanings mentioned previously and which are used as starting materials for process (c), are obtained by reaction of an o-phenylenediamine derivatives of the formula II with cyanogen bromide or cyanamide in hydrochloric acid in a solvent such as water, ethanol or dioxane.

To carry out process (c), a 2-aminobenzimidazole derivative of the formula VI is advantageously reacted with a dialkyl carbonate of the formula VII in a solvent, such as, for example, methanol, ethanol or in an excess of the dialkyl carbonate, in the presence of a strong base, such as, for example, sodium (m)ethylate or sodium hydride. The reaction temperature for this can be between −20° and +150° C., preferably between +20° and +100° C.

The new substituted phenylsulfonyloxybenzimidazolecarbamates according to the invention are valuable chemotherapeutic agents and are suitable for controlling parasitic diseases of humans and animals.

They are particularly effective against a large number of helminths, for example hemonchus, trichostrongylus, ostertagia, cooperia, chabertia, strongyloides, esophagostomum, hyostrongylus, ancylostoma, ascaris and heterakis, as well as fasciola. The efficacy for gastrointestinal strongylides, lung flukes and liver flukes, with which domestic and useful animals, in particular, are infested, is particularly pronounced. For this reason, the compounds according to the invention will be particularly used in veterinary medicaments.

Depending on the status of the case, the compounds of the formula I will be administered in doses between 0.1 and 50 mg per kg of body weight for 1 to 14 days. Pharmaceutical compositions, e.g. uncoated and coated tablets, capsules, powders, granules, suspensions or pastes which contain the active compounds together with customary auxiliaries or vehicles, such as starch, cellulose powder, talc, magnesium stearate, sugar, gelatin, calcium carbonate, finely divided silica, carboxymethylcellulose or similar substances, are suitable for oral administration.

The products of the processes have excellent efficacy not only on oral administration but they can also be administered parenterally. As pharmaceutical compositions solutions are suitable for parenteral administration, for example oily solutions which are produced using sesame oil, olive oil or synthetic triglycerides, where appropriate with the addition of, such as, for example, tocopherol as an antioxidant and/or using surface-active substances, such as sorbitan fatty acid esters. Aqueous suspensions produced using ethoxylated sorbitan fatty acid esters, where appropriate with the addition of thickeners, such as polyethylene glycol or carboxymethylcellulose, are also suitable.

For use as veterinary medicaments, the concentration of the active compounds according to the invention in the products prepared from them is preferably between 0.5 and 25 percent by weight; for use as human medicaments, the concentrations of the active compounds are preferably between 20 and 80 percent by weight.

The compounds of the formula I according to the invention surprisingly show a considerably more potent and wider anthelmintic activity than do the compounds known from U.S. Pat. No. 3,996,368, especially against *Fasciola hepatica*. Thus, for example, the compounds of the Examples 1–6 which follow show, at less than 30 mg/kg p.o., 90% activity for *Fasciola hepatica* in sheep and cattle, while the best compound according to the invention from U.S. Pat. No. 3,996,368, Example 22, shows no effect on cattle in this dose range.

PROCESS (a)

Example 1

Methyl 5-(4-fluorophenylsulfonyloxy)benzimidazole-2-carbamate 15.6 g of 2-amino-5-(4-fluorophenylsulfonyloxy)nitrobenzene (melting point 161° C.) in 75 ml of methanol and 75 ml of dimethylformamide are hydrogenated under atmospheric pressure with a catalytic amount of Raney nickel. After uptake of hydrogen is complete, the catalyst is filtered off with suction, washed with methanol and the filtrate is concentrated under reduced pressure.

The resulting 1,2-diamino-4-(4-fluorophenylsulfonyloxy)benzene is dissolved in 150 ml of methanol and 25 ml of glacial acetic acid. After addition of 15.5 g of N,N'-bis(methoxycarbonyl)-S-methylisothiourea, the mixture is heated to reflux, with stirring, for three hours. A precipitate starts to separate out after only about 10 minutes and, after cooling, it is filtered off with suction and washed with ethyl acetate. For purification, it is dissolved in hot dimethylformamide, methanol is added and, after cooling, the product is filtered off with suction, melting point 236° C., decomposition.

The following compounds of the formula I according to the invention are obtained in an analogous procedure using starting products modified appropriately:

2. From 2-amino-5-[3-(1,1,2,2-tetrafluoroethoxy)-phenylsulfonyloxy]nitrobenzene (melting point: resin) via 1,2-diamino-4-[3-(1,1,2,2-tetrafluoroethoxy)phenylsulfonyloxy]benzene, methyl 5-[3-(1,1,2,2-tetrafluoroethoxy)phenylsulfonyloxy]benzimidazole-2-carbamate, melting point 186° C.

3. From 2-amino-5-(4-ethylphenylsulfonyloxy)nitrobenzene (melting point 120° C.) via 1,2-diamino-4-(4-ethylphenylsulfonyloxy)benzene, methyl 5-(4-ethylphenylsulfonyloxy)benzimidazole-2-carbamate, melting point 180° C., decomposition.

4. From 2-amino-5-(4-isopropylphenylsulfonyloxy)nitrobenzene (melting point 105° C.) via 1,2-diamino-4-(4-isopropylphenylsulfonyloxy)benzene, methyl 5-(4-isopropylphenylsulfonyloxy)benzimidazole-2-carbamate, melting point 204° C.

5. From 2-amino-5-(4-propylphenylsulfonyloxy)nitrobenzene (melting point 96° C.) via 1,2-diamino-4-(4-propylphenylsulfonyloxy)benzene, methyl 5-(4-propylphenylsulfonyloxy)benzimidazole-2-carbamate, melting point 160° C., decomposition.

6. From 2-amino-5-(4-cyclohexylphenylsulfonyloxy)nitrobenzene (melting point 123° C.) via 1,2-diamino-4-(4-cyclohexylphenylsulfonyloxy)benzene, methyl 5-(4-cyclohexylphenylsulfonyloxy)benzimidazole-2-carbamate, melting point 254° C., decomposition.

7. From 2-amino-5-(3-fluorophenylsulfonyloxy)nitrobenzene (melting point 148° C.) via 1,2-diamino-4-(3-fluorophenylsulfonyloxy)benzene, methyl 5-(3-fluorophenylsulfonyloxy)benzimidazole-2-carbamate, melting point 233° C., decomposition.

8. From 2-amino-5-(3,4-difluorophenylsulfonyloxy)nitrobenzene (melting point 133° C.) via 1,2-diamino-4-(3,4-difluorophenylsulfonyloxy)benzene, methyl 5-(3,4-difluorophenylsulfonyloxy)benzimidazole-2-carbamate, melting point 223° C., decomposition.

9. From 2-amino-5-(2,4-difluorophenylsulfonyloxy)nitrobenzene via 1,2-diamino-4-(2,4-difluorophenylsulfonyloxy)benzene, methyl 5-(2,4-difluorophenylsulfonyloxy)benzimidazole-2-carbamate, melting point 248° C., decomposition.

10. From 2-amino-5-(4-bromophenylsulfonyloxy)nitrobenzene (melting point 165° C.) via 1,2-diamino-4-(4-bromophenylsulfonyloxy)benzene, methyl 5-(4-bromophenylsulfonyloxy)benzimidazole-2-carbamate, melting point 234° C., decomposition.

11. From 2-amino-5-(2-fluorophenylsulfonyloxy)nitrobenzene (melting point 124° C.) via 1,2-diamino-4-(2-fluorophenylsulfonyloxy)benzene, methyl 5-(2-fluorophenylsulfonyloxy)benzimidazole-2-carbamate, melting point 254° C., decomposition.

12. From 2-amino-5-[3,5-bis(trifluoromethyl)phenylsulfonyloxy]nitrobenzene (melting point 154° C.) via 1,2-diamino-4-[3,5-bis(trifluoromethyl)phenylsulfonyloxy]benzene, methyl 5-[3,5-bis(trifluoromethyl)phenylsulfonyloxy]benzimidazole-2-carbamate, melting point 258° C., decomposition.

13. From 2-amino-5-(3-bromo-4-fluorophenylsulfonyloxy)nitrobenzene via 1,2-diamino-4-(3-bromo-4-fluorophenylsulfonyloxy)benzene, methyl 5-(3-bromo-4-fluorophenylsulfonyloxy)benzimidazole-2-carbamate, melting point 257° C., decomposition.

14. From 2-amino-5-(3-chloro-4-fluorophenylsulfonyloxy)nitrobenzene via 1,2-diamino-4-(3-chloro-4-fluorophenylsulfonyloxy)benzene, methyl 5-(3-chloro-4-fluorophenylsulfonyloxy)benzimidazole-2-carbamate, melting point 259° C., decomposition.

15. From 2-amino-5-(4-cyclopentylphenylsulfonyloxy)nitrobenzene via 1,2-diamino-4-(4-cyclopentylphenylsulfonyloxy)benzene, methyl 5-(4-cyclopentylphenylsulfonyloxy)benzimidazole-2-carbamate, melting point 187° C., decomposition.

16. From 2-amino-5-(4-cycloheptylphenylsulfonyloxy)nitrobenzene via 1,2-diamino-4-(4-cycloheptylphenylsulfonyloxy)benzene, methyl 5-(4-cyclohep-tylphenylsulfonyloxy)benzimidazole-2-carbamate, melting point 157° C.

Example 17

Methyl 5-(4-fluorophenylsulfonyloxy)benzimidazole-2-carbamate 9 g of methyl chloroformate and 20 ml of 33% strength sodium hydroxide solution are added to a solution of 4.2 g of cyanamide in 20 ml of water. The mixture is then stirred for 1.5 hours at 30°–35° C. A solution of 22.6 g of 1,2-diamino-4-(4-fluorophenylsulfonyloxy)-benzene (see Example 1) in 200 ml of isopropanol is added to this solution and the temperature is raised to 80° C. After adding 30 ml of glacial acetic acid, the reaction mixture is heated at about 90° C. for 3 to 4 hours. After cooling, the product is filtered off with suction and washed with isopropanol and water. For purification, it is dissolved in hot dimethylformamide, methanol is added and, after cooling, the product is filtered off with suction, melting point 236° C., decomposition.

The compounds of the formula I according to the invention from Examples 2 to 16 are also obtained in analogy to Example 17 using appropriately modified starting materials.

Example 18

Methyl 5-[3-(1,1,2,2-tetrafluoroethoxy)phenylsulfonyloxy]benzimidazole-2-carbamate A solution of 15.6 g of methyl N-dichloromethylenecarbamate in 50 ml of methylene chloride is added slowly, with stirring, to a mixture of 38 g of 1,2-diamino-4-[3-(1,1,2,2-tetrafluoroethoxy)phenylsulfonyloxy]benzene (see Example 2), 20.2 g of triethylamine and 300 ml of methylene chloride at a temperature of about 20° C. The mixture is stirred for one hour and the precipitate is filtered off with suction and washed with diisopropyl ether. For purification, it is recrystallized from methanol, melting point 186° C.

The compounds of the formula I according to the invention from Examples 1 and 3 to 16 are also obtained in analogy to Example 18 using appropriately modified starting materials.

Example 19

Methyl 5-(4-propylphenylsulfonyloxy)benzimidazole-2-carbamate 30.6 g of 1,2-diamino-4-(4-propylphenylsulfonyloxy)-benzene (see Example 5) and 17.9 g of methyl N-[bis(-methylthio)methylene]carbamate in 200 ml of tetrahydrofuran are heated to reflux for four hours. After cooling, the precipitate is filtered off with suction and washed with diisopropyl ether. For purification, it is dissolved in hot dimethylformamide, methanol is added and, after cooling, the product is filtered off with suction, melting point 160° C., decomposition.

The compounds of the formula I according to the invention from Examples 1 to 4 and 6 to 16 are also obtained in analogy to Example 19 using appropriately modified starting materials.

PROCESS (b)

Example 20

Methyl 5-(4-fluorophenylsulfonyloxy)benzimidazole-2-carbamate 2.8 ml of triethylamine are added dropwise, with stirring, to 2.07 g of methyl 5-hydroxybenzimidazole-2-carbamate and 1.94 g of 4-fluorobenzenesulfonyl chloride at about 10° C. The mixture is then stirred at room temperature for 2 h, 100 ml of 2N acetic acid are added while cooling, and the resulting precipitate is filtered off with suction, washed with water and dried. Melting point 236° C., decomposition, from dimethylformamide/methanol.

The starting material is obtained as follows:

Methyl 5-hydroxybenzimidazole-2-carbamate 7.7 g of 4-amino-3-nitrophenol are hydrogenated in methanol with Raney nickel/H$_2$ at atmospheric pressure. After uptake of hydrogen is complete, the catalyst is filtered off with suction and the solution is concentrated to about 150 ml. 25 ml of glacial acetic acid and 12.4 g of N,N'-bis(methoxycarbonyl)-S-methylisothiourea are added and the mixture is heated to reflux, with stirring, for 3 h. The solution is concentrated, vigorously stirred with diisopropyl ether and the solid is filtered off with suction. For purification, it is recrystallized from ethyl acetate, melting point 300° C., incipient decomposition.

The compounds of the formula I according to the invention from Examples 2–16 are also obtained in analogy to Example 20 using appropriately substituted benzenesulfonyl halides of the formula V.

PROCESS (c)

Example 21

Methyl 5-(4-fluorophenylsulfonyloxy)benzimidazole-2-carbamate 1.1 g of sodium methylate in 25 ml of absolute toluene and 3.1 g of 2-amino-5-(4-fluorophenylsulfonyloxy)benzimidazole and 1.0 g of dimethyl carbonate are slowly heated, with stirring, to 120° C. and kept at this temperature for 4 h. After cooling, the mixture is concentrated under reduced pressure and, after addition of water, extracted with methylene chloride/methanol (9:1 vol/-vol). After concentrating, chromatography on silica gel is carried out using the same solvent mixture. The product is obtained from the appropriate fractions by precipitation with diisopropyl ether. It is filtered off with suction, washed with diisopropyl ether and dried; melting point 236° C., decomposition.

The starting material is obtained as follows:

2-Amino-5-(4-fluorophenylsulfonyloxy)benzimidazole 14.1 g of 1,2-diamino-4-(4-fluorophenylsulfonyloxy)-benzene (see Example 1) and 5.8 g of cyanogen bromide in 150 ml of methanol are heated to reflux for 6 h, then the mixture is cooled and concentrated. The residue is dissolved in water, and ammonia is added with cooling. The precipitated 2-aminobenzimidazole derivative is filtered off with suction, washed with water, dried and recrystallized from ethyl acetate and diisopropyl ether, with the addition of active charcoal; melting point 192° C.

The compounds of the formula I according to the invention from Examples 2–16 are also obtained in analogy to Example 21 using appropriately substituted 2-aminobenzimidazoles of the formula VI.

We claim:
1. A phenylsulfonyloxybenzimidazolecarbamate of the formula I

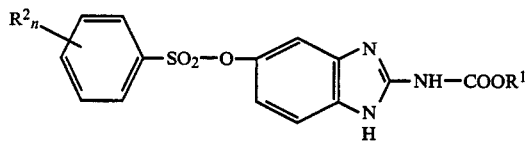

in which $R^1$ denotes straight-chain or branched alkyl having 1–4 carbon atoms, n denotes 1 or 2, and the individual substituents $R^2$, independently of one another, denote 1,1,2,2-tetrafluoroethoxy, cycloalkyl having 3–8 carbon atoms or 4-fluoro.

2. A phenylsulfonyloxybenzimidazolecarbamate of the formula I in claim 1 in which $R^1$ denotes methyl, n denotes 1 or 2, and $R^2$ denotes 1,1,2,2-tetrafluoroethoxy, cycloalkyl having 5, 6 or 7 carbon atoms or 4-fluoro.

3. Pharmaceutical composition for combating helminths which contains an effective amount of a substituted phenylsulfonyloxybenzimidazolecarbamate of the formula I in claim 1, in admixture or conjunction with a customary auxiliary or vehicle.

4. Method of treating a patient or animal suffering from infection by helminths by administering an effective amount of a substituted phenylsulfonyloxybenzimidazolecarbamate of the formula I in claim 1.

5. Pharmaceutical composition for combating helminths in humans which contains an effective amount of a substituted phenylsulfonyloxybenzimidazolecarbamate of the formula I in claim 1, in admixture or conjunction with a customary auxiliary or vehicle, the concentration of the active component being in the range from 20 to 80% by weight.

6. Pharmaceutical composition for combating helminths in animals which contains an effective amount of a substituted phenylsulfonyloxybenzimidazolecarbamate of the formula I in claim 1, in admixture or conjunction with a customary auxiliary or vehicle, the concentration of the active component being in the range from 0.5 to 25% by weight.

7. A phenylsulfonyloxybenzimidazolecarbamate according to the formula I in claim 1 in which $R^1$ denotes methyl.

8. A phenylsulfonyloxybenzimidazolecarbamate according to the formula I in claim 1 in which $R^2$ represents 4-fluoro.

9. A phenylsulfonyloxybenzimidazolecarbamate according to the formula I in claim 1 in which $R^2$ represents 1,1,2,2-tetrafluoroethoxy.

10. A phenylsulfonyloxybenzimidazolecarbamate according to the formula I in claim 1 in which $R^2$ represents cycloalkyl having 5, 6 or 7 carbon atoms.

11. A phenylsulfonyloxybenzimidazolecarbamate according to the formula I in claim 1 in which $R^1$ denotes methyl and $R^2$ represents 1,1,2,2-tetrafluoroethoxy.

12. A phenylsulfonyloxybenzimidazolecarbamate according to the formula I in claim 1 in which $R^1$ denotes methyl and $R^2$ represents cycloalkyl having 5, 6 or 7 carbon atoms.

13. Methyl 5-(4-fluorophenylsulfonyloxy)benzimidazole-2-carbamate.

14. Methyl 5-[3-(1,1,2,2-tetrafluoroethoxy)-phenylsulfonyloxy]benzimidazole-2-carbamate.

15. Methyl 5-(4-cyclohexylphenylsulfonyloxy)-benzimidazole-2-carbamate.

* * * * *